United States Patent [19]

Molacek et al.

[11] Patent Number: 5,303,704
[45] Date of Patent: Apr. 19, 1994

[54] MEDICAL ELECTRICAL LEAD

[75] Inventors: Richard L. Molacek, Maple Grove; Allan H. Jevne, Anoka; Peter J. Pohndorf, Stillwater; Kenneth E. Cobian, St. Anthony; Joseph F. Lessar, Coon Rapids; James E. Upton, New Brighton, all of Minn.

[73] Assignee: Medtronic, Inc., Minneapolis, Minn.

[21] Appl. No.: 994,756

[22] Filed: Dec. 22, 1992

[51] Int. Cl.⁵ .............................................. A61B 5/04
[52] U.S. Cl. ..................................... 128/642; 607/122
[58] Field of Search ............... 128/786, 783, 784, 785, 128/642; 607/115, 116, 119, 122

[56] References Cited

U.S. PATENT DOCUMENTS

| | | |
|---|---|---|
| 3,348,548 | 10/1967 | Chardack . |
| 4,378,020 | 3/1983 | Nappholz et al. ............ 128/419 PG |
| 4,595,012 | 6/1986 | Webler et al. ........................ 128/786 |
| 4,608,986 | 9/1986 | Beranek ............................. 128/786 |
| 4,651,751 | 3/1987 | Swendson et al. .................. 128/786 |
| 4,718,423 | 1/1988 | Willis et al. ......................... 128/786 |
| 5,029,585 | 7/1991 | Lieber et al. ........................ 128/786 |
| 5,092,333 | 3/1992 | Tsuchida et al. ................... 128/786 |

OTHER PUBLICATIONS

Advertisement in Medical Product Manufacturing News, Jul./Aug., 1990 by Putnam Plastics Corporation.

Primary Examiner—William E. Kamm
Assistant Examiner—Kennedy J. Schaetzle
Attorney, Agent, or Firm—Reed A. Duthler; Harold R. Patton

[57] ABSTRACT

An implantable multi-lumen, multi-conductor lead for use with an implantable medical device. The completed lead is an assembly of a polymeric lead body with several coiled conductors inserted into the lead body. The lead body includes several lumens having a generally rounded-corner triangular or "pie-shaped" cross-section. The conductors do not fill the lumens, and only contact the inner walls of the lumens at discrete points, rather than for extended sections of or all of the circumference of the conductors. Preferably the coils are sized so that they fit loosely within the lumens.

8 Claims, 1 Drawing Sheet

MEDICAL ELECTRICAL LEAD

BACKGROUND OF THE INVENTION

The present invention relates to an implantable multi-lumen multi-conductor lead for use with an implantable medical device.

Medical leads are used to transmit electrical signals to and from medical devices such as pacemakers. The lead body is usually made from a piece of polymeric tubing having a round cross-section exterior and a round cross-section lumen. Typically a coiled metallic electrical conductor having a round cross-section is placed in the lumen completely filing it. The tubing protects and insulates the conductor. The coiled conductor can usually receive a stylet to help position and place the lead during implantation. Such a lead is illustrated in U.S. Pat. No. 3,348,548.

Since both the conductor and lumen have a round shape with substantially equal diameters, assembly of the lead can be difficult due to friction between the conductor and lead. Because the lead body is flexible, and the conductor coils are substantially more rigid, this problem is not substantially reduced by the use of circular lumens slightly larger in diameter than the coils. In areas where the lead body is flexed, the result is still that the lumen wall will deform to contact a substantial percentage of the circumference of each individual coil. Assembly problems are exacerbated when this form of lead construction is extended to small diameter, multi-conductor, multi-lumen designs.

Various alternative designs have been proposed to form multi-lumen leads. U.S. Pat. No. 4,608,986 discloses a lead having an array of round lumens, but using essentially straight, uncoiled conductors. Multi-lumen tubing having non-round lumens is known in the art. See for example the advertisement by Putnam Plastics Corporation in the July/August 1990 issue of *Medical Product Manufacturing News*. For example, multi-lumen tubing having pie-shaped lumens is used to manufacture thermodilution catheters, which may include a twisted wire pair in one of the lumens, connected to a thermistor.

SUMMARY OF THE INVENTION

The present invention is an implantable multi-lumen, multi-conductor lead for use with an implantable medical device. The lead includes an insulative lead body and at least one conductor mounted within the lead body. The lead body includes at least one non-round lumen. More typically several non-round lumens will be located in a pattern within the interior of the lead body. The preferred non-round lumen exhibits a generally rounded-corner triangular or "pie-shaped" cross-section. The conductors are located within the lumens and are coiled conductors, typical of those known to the art. The configurations of the lumens and conductors result in the conductors contacting the inner walls of the lumens at discrete points around the circumferences of the conductors, rather than for extended sections of or all of the circumferences of the conductors as in typical prior art leads having round lumens and coiled conductors. Preferably the coil is sized so that it fits loosely within the lumen, with the result that in any individual coil of the conductor will contact the interior surface of the lumen at no more than two points.

The limited points of contact between the conductor and the lumen reduce frictional resistance to relative movement of the lead body and the conductors, which in turn enhances the flexibility and stretch characteristics of the lead. The reduced frictional resistance to relative movement also reduces the difficulty of assembly of the lead by making the step of insertion of the coiled conductor substantially easier.

BRIEF DESCRIPTION OF THE DRAWINGS

In the drawings where like numerals refer to like components throughout several views.

DETAILED DESCRIPTION OF THE PREFERRED EMBODIMENT

Figure 1:
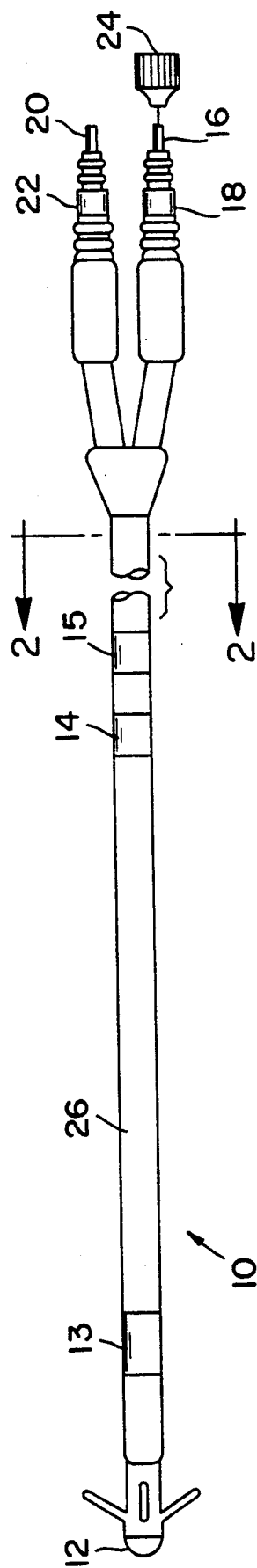
FIG. 1 is a diagram of a lead which incorporates a preferred embodiment of the present invention.

FIG. 1 is a diagram of a lead assembly 10, which incorporates a preferred embodiment of the invention. The lead body 26 carries four electrodes including ventricular electrodes 12 and 13 and atrial electrodes 14 and 15. Within the lead body are four conductors, one coupled to each of the electrodes and extending proximally to a corresponding electrical connector. The proximal end of the lead assembly 10 has a dual in-line connector assembly including connector pin 16, coupled to electrode 12, connector ring 18, coupled to electrode 13, connector pin 20, coupled to electrode 14 and connector ring 22, coupled to electrode 15. A stylet 24 may be inserted into the lead through pin 16 to stiffen it as an aid to implantation.

Lead body 26 is preferably fabricated of silicone rubber, polyurethane or other implantable polymer. Electrodes 12, 13, 14 and 15 are preferably fabricated of platinum alloy or other biocompatible metal. Connectors 16, 18, 20, 22 are preferably fabricated of stainless steel or other biocompatible metal.

As illustrated the lead includes electrodes which may serve as means for delivery of stimulation pulses and as means for sensing physiological electrical signals. It should also be understood that a lead according to the present invention may also include means for sensing other physiological parameters, such as pressure, oxygen saturation, temperature or pH. The lead may include electrodes only, other physiologic sensors only or a combination of both.

Figure 2:
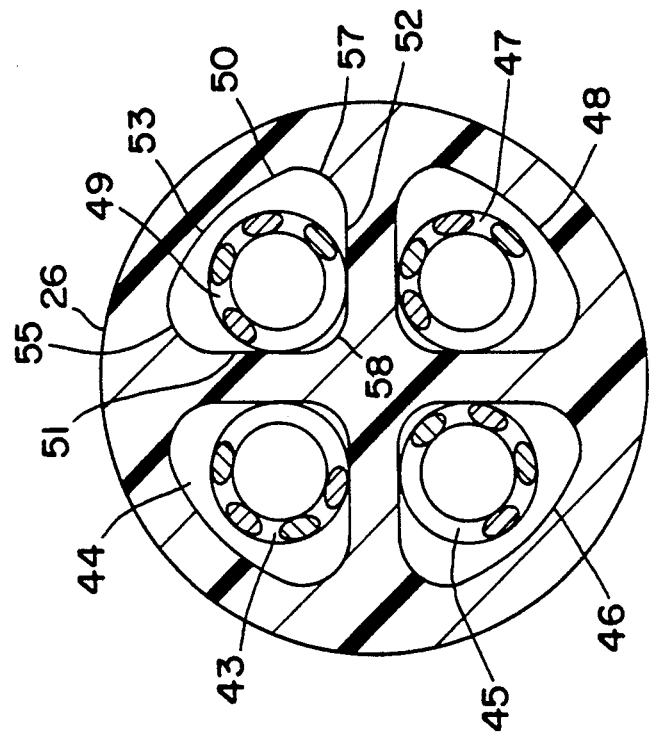
FIG. 2 is a cross-sectional view of the lead body of the lead shown in FIG. 1.

FIG. 2 is a cross-section through the lead body 26. In this view, it can be seen that lead body 29 is provided with four pie-shaped or generally triangular lumens. The first lumen 44 contains a first coiled conductor 43. The second lumen 46 contains a second coiled conductor 45. The third lumen 48 contains a third coiled conductor 47. The fourth lumen 50 contains a fourth coiled conductor 49. The conductors 43, 45, 47 and 49 are preferably fabricated of MP35N alloy or other biocompatible metal. In the drawing each coiled conductor is shown as a multi-filar coil. However monofilar coils are useful as well. One of the four conductors is coupled to pin 16 and also serves to receive a stylet.

The lead body may employ the multi-lumen configuration illustrated over its entire length, with two of the lumens unused distal to electrodes 14 and 15. Alternatively, a transition to a lead body having a coaxial or side by side two-lumen configuration as typically used in bipolar pacing leads may occur at or distal to electrodes 14 and 15.

As seen in cross section, the representative fourth lumen 50 has three walls each having a radius of curvature substantially greater than the radius of curvature of the conductor coil. These walls include two substantially planar walls 51 and 52 each extending along a radius of said body and an outer curved wall 53, extending along the outer circumference of the lead body. The walls are joined to one another along corners 55, 57 and 58 each of which have a radius of curvature substantially less than the radius of curvature of the conductor coils, in seen in this cross section.

As illustrated, contact between a coil of a conductor and the inner surface of a lumen will be limited to those portions of the inner surfaces of the lumen which have a substantially greater radius of curvature than the conductor coil. Contact will thus be limited to discrete points of contact, rather than along substantial lengths of the individual coils, as would occur in prior leads employing circular coils and circular lumens of similar sizes. Contact will occur only along walls 51, 52 and 53, and not in corners 55, 57 and 59. Along the length of the lead, individual coils will contact various points on all three walls 51, 52 and 53.

A decrease in the area of contact between the coiled conductor and the lumen could also be obtained by simply employing a circular lumen of substantially larger diameter than the conductor coil, to provide a single inner wall surface having a substantially greater radius of curvature than the coil. However, this approach would require a lumen of substantially greater cross section than a lumen according to the present invention. As the minimum wall thickness for adequate electrical isolation between the lumens imposes a design constraint on all such leads, increases in diameter of a circular lumen result in increases in achievable minimum lead diameter. The present invention avoids this problem, as the improved lumen shape can be accomplished without increasing the overall diameter of the lead.

The non-round lumen shape also allows a lead body to be fabricated using less material than a corresponding lead body employing circular lumens. This not only reduces the cost of extruding the lead body but also allows the use of relatively stiffer plastics without as great a compromise in the overall flexibility of the lead, due to the relative reduction in the cross sectional area of the plastic in the lead body. For example the non-round lumen design would allow substitution of 55D Pellethane for 80A Pellethane, providing the enhanced biostability of the 55D polyurethane without as severe an increase in stiffness as would occur if the lead employed mare traditional round lumens.

The embodiment illustrated above is intended to be exemplary, rather than limiting, with regard to the following claims.

What is claimed is:

1. A medical, electrical lead, comprising:
   an elongated lead body having a first lumen, extending longitudinally along said lead body; and
   a coiled conductor located loosely within and extending longitudinally along said lumen, the individual coils of said coiled conductor having a first radius of curvature, as measured in a cross section through said lead body; and
   wherein said lumen has a plurality of longitudinally extending inner wall surfaces each having a radius of curvature in excess of said first radius of curvature, as measured in said cross section, joined to one another by longitudinally extending corner surfaces each having a radius of curvature less than said first radius of curvature, as measured in said cross section.

2. A lead according to claim 1, wherein said lumen has three of said longitudinally extending inner wall surfaces each having a radius of curvature in excess of said first radius of curvature, as measured in said cross section, joined to one another by longitudinally extending corner surfaces each having a radius of curvature less than said first radius of curvature, as measured in said cross section.

3. A lead according to claim 1 claim 2 further comprising an electrical connector coupled to a first end of said coiled conductor.

4. A lead according to claim 1 further comprising a means for sensing a physiological parameter, coupled to said coiled conductor.

5. A lead according to claim 4 wherein said sensing means comprises an electrode coupled to said coiled conductor.

6. A medical, electrical lead, comprising:
   an elongated lead body having a plurality of lumens, extending longitudinally along said lead body; and
   a coiled metal conductor located loosely within and extending longitudinally along each of said plurality of lumens, the individual coils of said coiled conductors having a first radius of curvature, as measured in a cross section through said lead body; and
   wherein said lumen has a plurality of longitudinally extending inner wall surfaces each having a radius of curvature in excess of said first radius of curvature, as measured in cross section having joined to one another by longitudinally extending corner surfaces each having a radius of curvature less than said first radius of curvature, as measured in cross section.

7. A lead according to claim 6 wherein each of said plurality of lumens has three of said longitudinally extending inner wall surfaces each having a radius of curvature in excess of said first radius of curvature, as measured in said cross section, joined to one another by longitudinally extending corner surfaces each having a radius of curvature less than said first radius of curvature, as measured in said cross section.

8. A lead according to claim 7 wherein each of said plurality of lumens has two of said longitudinally extending inner wall surfaces, each generally straight in said cross section, and a third said longitudinally extending inner wall surface, curved in said cross section, and wherein said third walls are located around the circumference of said lead body.

* * * * *